United States Patent
Ross et al.

(10) Patent No.: US 12,014,817 B2
(45) Date of Patent: *Jun. 18, 2024

(54) SYSTEMS AND METHODS FOR VISUALIZING AND MANAGING TELEPRESENCE DEVICES IN HEALTHCARE NETWORKS

(71) Applicant: TELADOC HEALTH, INC., Purchase, NY (US)

(72) Inventors: Scott Ross, Santa Barbara, CA (US); Kelton Temby, Santa Barbara, CA (US); Jonathan Southard, Santa Barbara, CA (US); Dan Habecker, Santa Barbara, CA (US); Michael Chan, Santa Barbara, CA (US); Timothy C. Wright, Santa Barbara, CA (US); Charles S. Jordan, Santa Barbara, CA (US); Joshua A. Bouganim, Valley Village, CA (US)

(73) Assignee: TELADOC HEALTH, INC., Purchase, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/555,591

(22) Filed: Dec. 20, 2021

(65) Prior Publication Data
US 2022/0115118 A1  Apr. 14, 2022

Related U.S. Application Data

(63) Continuation of application No. 15/012,636, filed on Feb. 1, 2016, now Pat. No. 11,205,510, which is a
(Continued)

(51) Int. Cl.
*G16H 40/20* (2018.01)
*G16H 40/67* (2018.01)
*G16Z 99/00* (2019.01)

(52) U.S. Cl.
CPC .......... *G16H 40/20* (2018.01); *G16H 40/67* (2018.01); *G16Z 99/00* (2019.02)

(58) Field of Classification Search
CPC ........ G16H 40/20; G16H 40/67; G16Z 99/00; H04M 11/04; H04M 2242/04; H04W 4/90; H04W 76/50; G08B 25/106
(Continued)

(56) References Cited

U.S. PATENT DOCUMENTS 8,666,771 B2 * 3/2014 Roesch ............... G16H 40/20 705/2
11,205,510 B2 * 12/2021 Ross .................. G16H 40/20
(Continued)

*Primary Examiner* — Maria El-Zoobi

(57) ABSTRACT

Disclosed herein are various embodiments of systems and methods for visualizing, analyzing, and managing telepresence devices operating in a telepresence network of healthcare facilities. The visualization and management system for telepresence devices may display a first viewing level that includes a geographical representation of the location of various telepresence devices. A user may selectively view a global view of all telepresence devices, telepresence devices within a particular region, and/or the details of a particular telepresence device. A user may also access a viewing level of a network of healthcare facilities. The user may view, analyze, and/or manage the healthcare network, telepresence device network, individual telepresence devices, connection rules, and/or other aspects of the healthcare network using the geographical visualization and management tool described herein.

20 Claims, 15 Drawing Sheets

Related U.S. Application Data continuation of application No. 13/444,106, filed on Apr. 11, 2012, now Pat. No. 9,251,313.

(58) Field of Classification Search
USPC .......................... 705/2; 379/52; 455/404.01
See application file for complete search history.

(56) References Cited

U.S. PATENT DOCUMENTS

| | | | | |
|---|---|---|---|---|
| 2006/0238379 | A1* | 10/2006 | Kimchi | G01C 21/26 340/995.1 |
| 2009/0284348 | A1* | 11/2009 | Pfeffer | G08B 25/006 340/7.3 |
| 2010/0131103 | A1* | 5/2010 | Herzog | B25J 5/007 901/1 |
| 2010/0251158 | A1* | 9/2010 | Geppert | H04L 12/1822 715/771 |
| 2011/0117878 | A1* | 5/2011 | Barash | G08B 25/016 340/539.12 |
| 2013/0002805 | A1* | 1/2013 | Andresen | H04N 7/147 348/14.07 |

\* cited by examiner

SYSTEMS AND METHODS FOR VISUALIZING AND MANAGING TELEPRESENCE DEVICES IN HEALTHCARE NETWORKS

TECHNICAL FIELD

This disclosure relates to managing telepresence devices in healthcare networks. More specifically, this disclosure provides various visualization and management systems for use with telepresence devices, healthcare networks, and associated information.

BRIEF DESCRIPTION OF THE DRAWINGS

Non-limiting and non-exhaustive embodiments of the disclosure are described herein, including various embodiments of the disclosure illustrated in the figures listed below.

Figure 1:
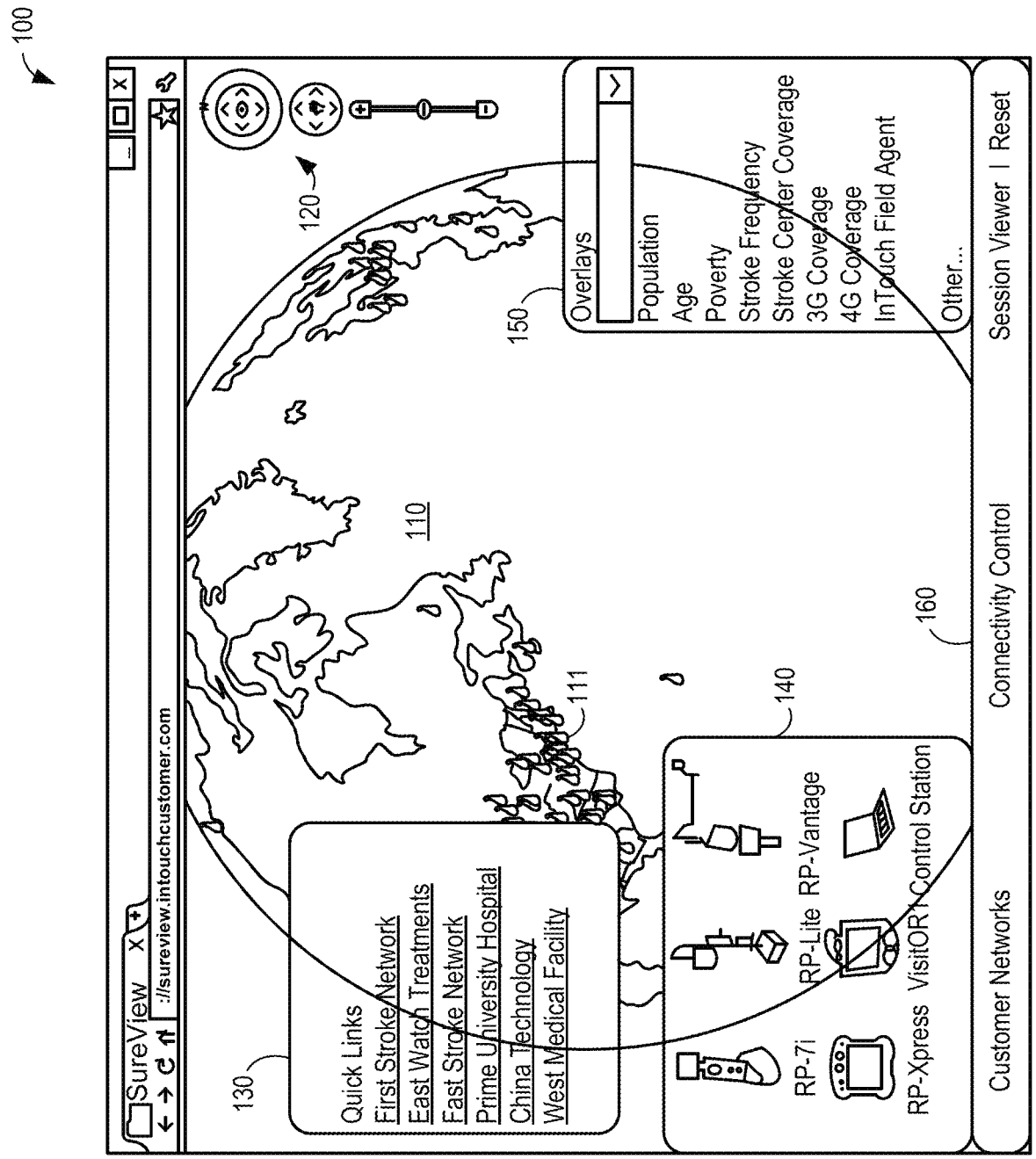
FIG. 1 illustrates a viewing level including a geographical representation of the world, shortcut links to various geographical locations, selectable icons associated with various device types, a navigation input panel, and selectable overlays.

The described features, structures, and/or characteristics of the systems and methods described herein may be combined in any suitable manner in one or more alternative embodiments, and may differ from the illustrated embodiments.

DETAILED DESCRIPTION

The present disclosure provides various systems and methods for visualizing and managing telepresence devices within healthcare networks and facilities. Using the presently described visualization and management tool, users may more efficiently visualize, analyze, and actively manage various aspects of a telepresence healthcare network. In some embodiments, a user may view a geographical representation of the relative location of each of a plurality of telepresence devices in a telepresence network.

Healthcare facilities may include telemedicine technologies, such as telepresence devices in a telepresence network, that allow remote healthcare practitioners to provide services to patients and/or other healthcare practitioners in remote locations. For example, a remote medical professional may be a neurologist practicing in a major hospital who may, via telepresence devices, provide services and consultations to patients and other medical professionals in hospitals located in rural areas that may otherwise not have a neurologist on staff.

The telepresence devices may operate as part of a telepresence network associated with one or more healthcare networks. Each healthcare network may include one or more healthcare facilities (e.g., hospitals, rehabilitation facilities, and long-term care facilities) that each have one or more telepresence devices. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

A visualization and management system for telepresence devices may be configured to display a first viewing level that includes a geographical representation of the location of various telepresence devices. The viewing level may include all telepresence devices, those within predefined geographical boundaries, those associated with a particular healthcare network, or those associated with a particular healthcare facility. The telepresence devices and/or healthcare facilities may also be displayed as hub devices/facilities and spoke devices/facilities. The various interconnections between the hubs and spokes may be selectively displayed.

A navigation control panel may allow a user to navigate within the geographical representation. For example, the navigation panel may allow for panning, tilting, scrolling, compass alignments, and/or other navigational options. Additionally, the field of view may be dynamically modified based on a user's selection. For example, the field of view may be controlled by a zooming panel or icon, or alternatively may be dynamically adjusted based on other navigational or icon selections. The information associated with the displayed telepresence devices and/or healthcare facilities may be limited or expanded based on the number of telepresence devices and/or healthcare facilities currently displayed in the selected field of view. In some embodiments, shortcuts may allow a user to quickly navigate to a specific geographical location, to a specific medical facility, to a specific medical network, and/or to a specific telepresence device.

The first viewing level may include various icons, panels, buttons, and/or other selectable options configured to allow a user to select one or more alternative viewing levels. For example, a device detail request module may allow a user to submit a detail request in order to view detailed information associated with one or more telepresence devices, healthcare facilities, and/or healthcare practitioners shown on the geographical representation. A user may request additional details by selecting a particular telepresence device and/or healthcare facility. In some embodiments, additional details may be presented when a user mouses over a device/facility. The mouse-over may cause a pop-up overlay to appear displaying additional details associated with the device/facility. The details associated with one or more telepresence devices may include the connection strength, the number of active sessions, a history of technical problems, a history of session activity, shipping information associated with a telepresence device, information associated with a software update, information associated with a firmware update, a serial number, a model number, a battery level, a date the telepresence device last reported, a time the telepresence device last reported, historical session data, a registered peripheral, a licensed application, a total utilization time, an average session duration, a duration of a particular session, a start time of a particular session, an end time of a particular session, a Quality of Service (QoS) for one or more sessions, a current available bandwidth, a bandwidth availability with respect to time, a current location of a telepresence device, and historical locations of a telepresence device with respect to time.

Similarly, the details associated with one or more healthcare facilities may include a number of active sessions, a number of active telepresence devices, a connection strength of telepresence devices, a connection between two or more telepresence devices, a location of a telepresence device, information from a StrokeRESPOND application, a door-to-needle time, a door-to-balloon time, t-PA contraindication and warning information, a healthcare practitioner response time, and a call center response time.

Additionally, details associated with a particular telepresence device, healthcare facility, healthcare network, and/or healthcare practitioner may include one or more connection rules. For example, connection rules may define where, when, and how a healthcare facility, healthcare network, and/or healthcare practitioner may access, view, monitor, and/or control a particular telepresence device or set of telepresence devices. The connection rules may also define who is granted access and what devices they can view. In some embodiments, a viewing level displaying one or more connection rules may allow a user to manage and/or configure the various connection rules between devices, facilities, and/or practitioners. In one embodiment, connection rules may be managed using drag-and-drop actions between devices, facilities, and/or practitioners.

Some of the viewing levels may include geographical representations constrained by particular geographical boundaries, the extent of a healthcare network, or the location of associated telepresence devices. Some of the viewing levels may include selectable overlays configured to overlay information on the geographical representations. Accordingly, a user may apply an informational overlay to a geographical representation that includes various healthcare facilities and/or telepresence devices.

Examples of overlays include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation as a heat map, as graphics, as pictures, as icons, as numbers, and/or as text.

In some embodiments, the informational overlay may be overlaid on the entire geographical representation. In other embodiments, the informational overlay may be overlaid on a portion of the geographical representation. For example, the informational overlay may only be overlaid on the portion of a geographical representation that corresponds to a geographical area serviced by a particular healthcare network, hospital, hub hospital, spoke hospital, telepresence device, support technician, and/or medical practitioner.

In some embodiments, a viewing level may include a geographical representation displaying the relative location of various telepresence devices. The viewing level may include various selectable device icons that each correspond to a particular type of telepresence device. The device icons may be used to toggle between displaying and not displaying the associated type of telepresence device. Accordingly, a user may toggle the device icons in order to view all of the control stations, but not the mobile telepresence units or the remote telepresence robots. Within the same viewing level, the user may toggle the device icons to view the remote telepresence robots and/or the mobile telepresence units, but not the control stations. Additional device icons may further differentiate between device types, models, vintages, active telepresence devices, inactive telepresence devices, and/or other characteristics of the various telepresence devices.

The visualization and management of telepresence networks may allow healthcare facilities, healthcare networks, healthcare practitioners, technical support personnel, and/or other users to improve patient care, provide enhanced telepresence services, reduce the costs associated with telepresence consultations, and/or otherwise improve existing technologies and systems. Suitable networks for use with the present visualization and management systems include any of a wide variety of physical infrastructures, protocols, connections, and encryption algorithms. According to various embodiments, networking practices may be implemented in order to comply with accepted healthcare standards and/or government regulations.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware. Accordingly, the various components, modules, systems, and/or features described herein may be embodied as modules within a system. Such a system may be implemented in software, firmware, hardware, and/or physical infrastructure.

Embodiments may also be provided as a computer program product including a non-transitory machine-readable medium having stored thereon instructions that may be used to program or executed on a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

FIG. 1 illustrates a global viewing level 100 of a geographical representation of the world 110. As illustrated, the global viewing level 100 may include a navigation panel 120 with various icons configured to allow a user to pan, rotate, tilt, and zoom within the global viewing level. For instance, a slider bar may be slid between a "−" sign and a "+" sign in order to control the field of view of the geographical representation 110. A wide field of view may include the entire globe, as illustrated, and a narrow field of view may be limited to a single telepresence device and/or healthcare facility. The global viewing level 100 may include various quick links 130. A user may use the quick links 130 to navigate to a specific location on the geographical representation 110 and/or automatically adjust the field of view.

The viewing level 100 may also include a panel 140 of device-type icons. By selecting a device icon in the panel 140, a user may choose whether or not the particular device type is displayed on the geographical representation 110. For example, the illustrated viewing level 100 displays icons representing various telepresence devices on the geographical representation 110. By toggling the device-type icons within the panel 140, a user may selectively view one or more types of telepresence devices and disable the display of the other types. Accordingly, a user may filter by telepresence device type.

Additionally, the viewing level 100 may include selectable overlays within an overlay panel 150. The selectable overlays may include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation 110 as a heat map, as graphics, as pictures, as icons, as numbers, and/or as text. A user may apply an overlay on geographical representation 110 in order to visualize the relationships between the information conveyed by the overlay, technical data, healthcare networks, and/or telepresence devices.

A lower panel 160 may include additional selectable icons and/or display information about the current session. For example, a reset icon may allow a user to reset or refresh the visualization and management system. A customer networks icon may allow the user to switch from a geographical representation of the relative location of telepresence devices to a geographical representation of the relative location of healthcare facilities and/or healthcare networks, or to a connectivity control panel.

For purposes of this disclosure, the selection of an icon within any of panels 130, 140, 150, and 160 may be considered a transition from the viewing level 100 to a different viewing level. Alternatively, the selection of some of the icons within panels 130, 140, 150, and/or 160 may display additional information, remove displayed information, and/or modify displayed information but remain within the same viewing level. The viewing level 100 illustrated in FIG. 1 may be displayed in a web browser, potentially using one or more plug-ins. Alternatively, the various viewing levels may be displayed and/or controlled in a stand-alone application or in any other suitable computing environment.

Figure 2:
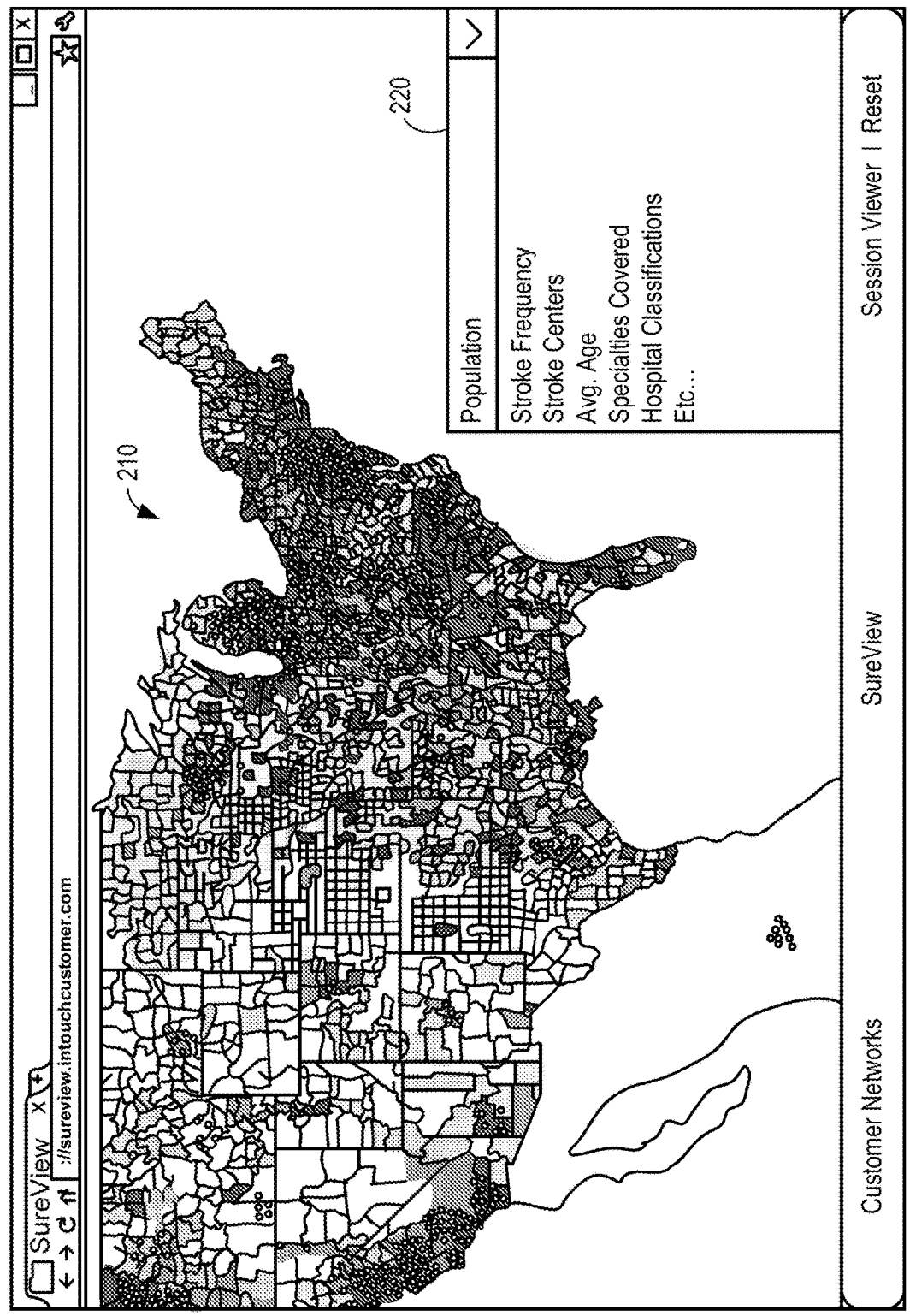
FIG. 2 illustrates a viewing level of a geographical representation of the United States with a population density overlay.

FIG. 2 illustrates a viewing level 200 with a narrower field of view showing a heat map overlaid on a geographical representation 210. The illustrated geographical representation 210 includes the continental United States. As illustrated, an overlay panel 220 may include various informational overlays that may be applied to the geographical representation 210. The overlays may be applied in any of a wide variety of manners, such as by applying a corresponding heat map, graphics, pictures, icons, numbers, and/or text. In the illustrated embodiment, the white dots on the geographical representation 210 may represent available telepresence devices.

The heat map overlay may correspond to a population density. Accordingly, it may be useful (e.g., to assess need or sales opportunities) to compare the population density across the continental United States to the location of available/existing telepresence devices. For instance, in the illustrated example, the population density near the border of Illinois and Iowa is relative high, and yet there is no telepresence device nearby. Accordingly, a sales opportunity or need may exist in that region.

Figure 3:
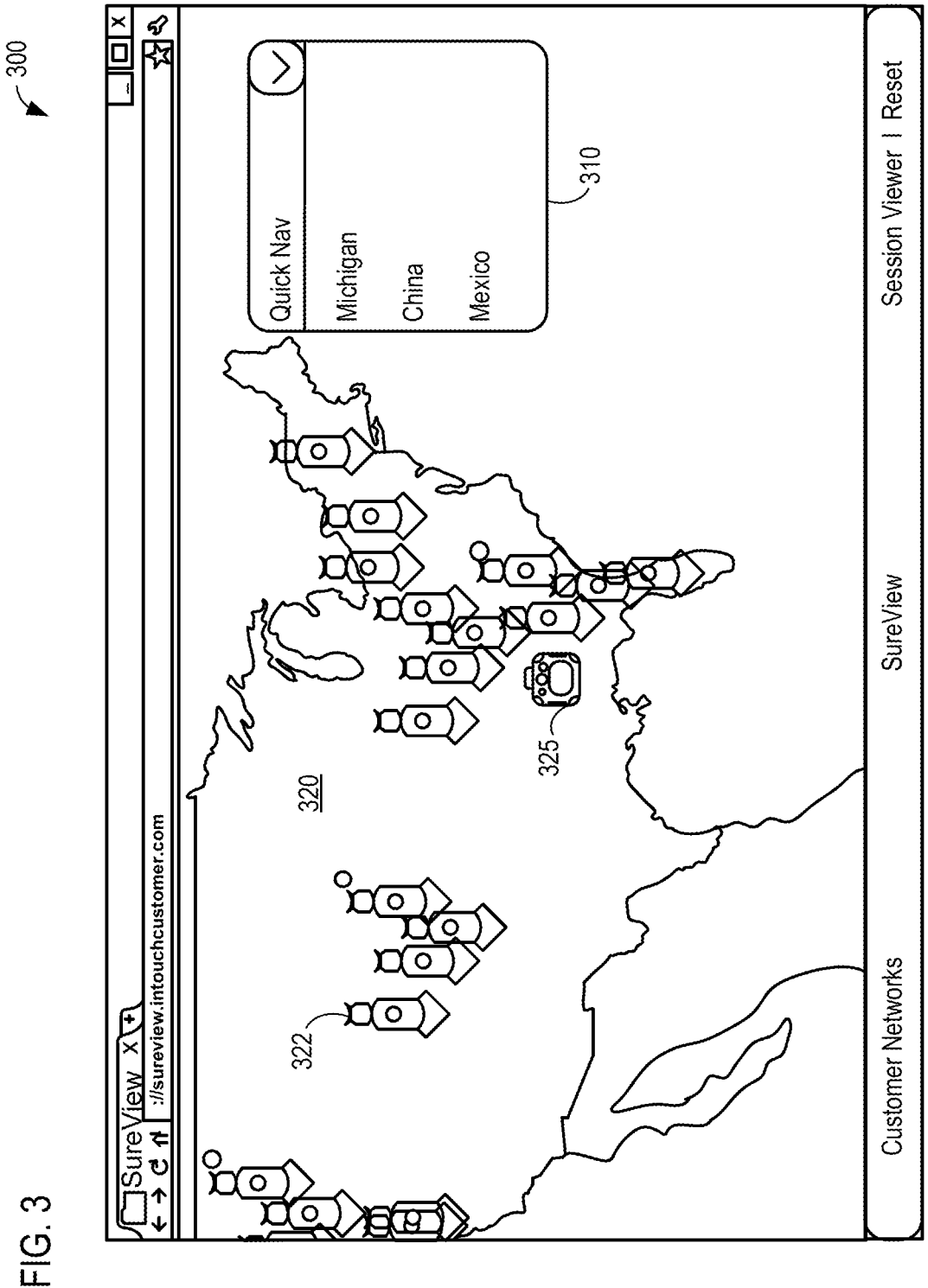
FIG. 3 illustrates a shortcut menu configured to allow for direct navigation to various locations within a geographical representation.

FIG. 3 illustrates a "Quick Nav" shortcut menu 310 configured to allow for direct navigation to a location within the geographical representation 320. The Quick Nav menu 310 may be customized and/or include various default locations. Any number of selectable locations may be included in the shortcut menu 310. Selecting a location within the shortcut menu 310 may pan, rotate, tilt, and/or zoom the window in order to frame the selected geographical location. The telepresence devices and/or healthcare facilities within the framed geographical representation 320 may be displayed as icons resembling corresponding types of telepresence devices and/or healthcare facilities. Alternatively, other symbols, icons, coloring, numbers, text, or markings may be utilized to display the relative location of various telepresence devices and/or healthcare facilities within the displayed geographical boundaries. In the illustrated embodiment, robotically controlled telepresence devices are illustrated with robot icon 322, and mobile telepresence units are illustrated with an icon 325 resembling the device type.

Figure 4B:
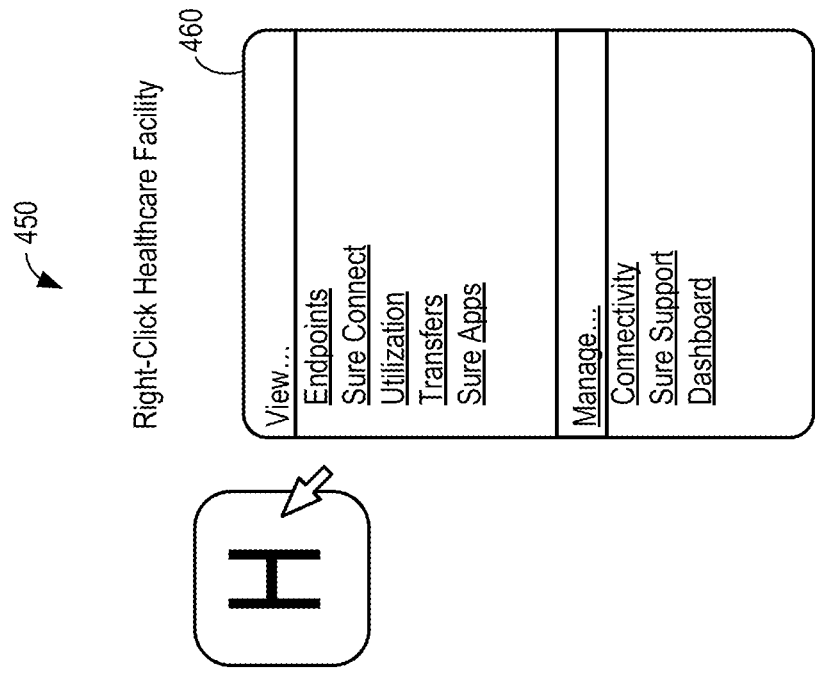
FIGS. 4A and 4B illustrate context-based detail request menus providing access to specific details based on the type of telepresence device and/or type of healthcare facility.
Figure 4A:
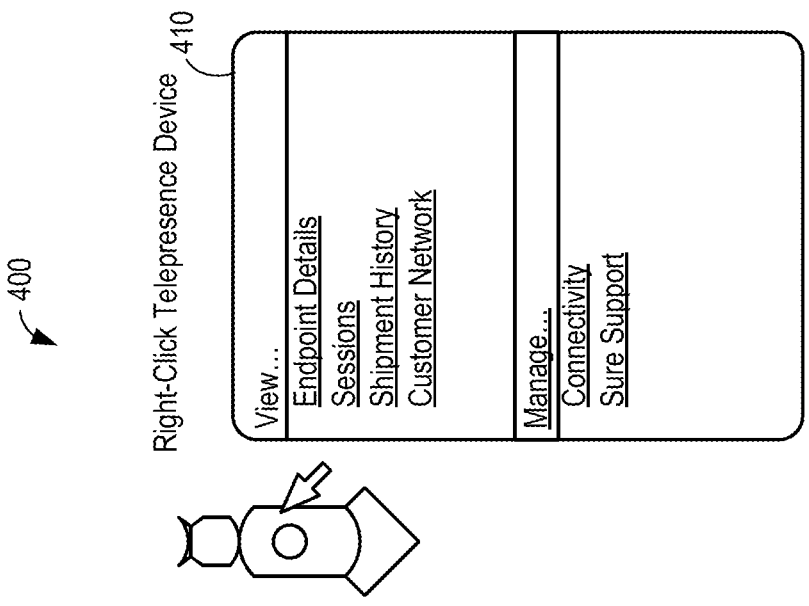

FIGS. 4A and 4B illustrate context-based detail request menus 400 and 450 providing access to specific details based on the type of telepresence device and/or type of healthcare facility. The detailed information, titles, names, and icons used in menus 400 and 450 may be modified or adapted for a particular application or need. As illustrated in FIG. 4A, by right-clicking (or through the use of another secondary selection method) on the robot icon, a user may select various viewing details or management details in panel 410. Detail requests may include information associated with telepresence devices, communication sessions, shipment history, and available networks. Additionally, a user may select various management details, such as connectivity and support. Different types of telepresence devices may include different detail selection options for viewing and/or managing. Moreover, the identity of the user may modify which selectable detail requests are available. For example, an administrator of a telepresence device may have more access than a low-level healthcare practitioner.

As illustrated in FIG. 4B, when a healthcare facility icon is right-clicked, a different detail request panel 460 may be displayed. The selectable detail requests within panel 460 may be based on the identity of the user, a characteristic of the user, the type of healthcare facility, and/or the types of available telepresence devices associated with the healthcare facility. As illustrated, a user may select to view additional details associated with endpoints (telepresence devices) associated with the healthcare facility, connection rules, utilization statistics of telepresence devices, transfer statistics, and other interfacing applications. Additionally, the user may select to manage details such as connectivity, support, and/or a dashboard of other informational details.

Hovering a mouse over a telepresence device icon and/or a healthcare facility icon (a mouse-over) may display one or more details about the specific device/facility. For example, a mouse-over may display the serial number of a telepresence device and the hospital with which it is associated. Additional information may be displayed via a mouse-over and/or by selecting the icon representing the device/facility.

Any of the selectable icons, panels, and/or options may be accessible in any of the viewing levels described herein. Specifically, the viewing level requests via navigation panels and/or shortcut menus (illustrated in FIGS. 1 and 3), the available overlays (illustrated in FIG. 2), and the detail request panels (illustrated in FIGS. 4A and 4B) may be available in the viewing level illustrated in FIG. 1. The exact depictions of icons, panels, geographical representations, and other specific details illustrated and/or described in conjunction with the figures are merely exemplary and may be modified, augmented, replaced, and/or eliminated for a particular application.

Figure 5:
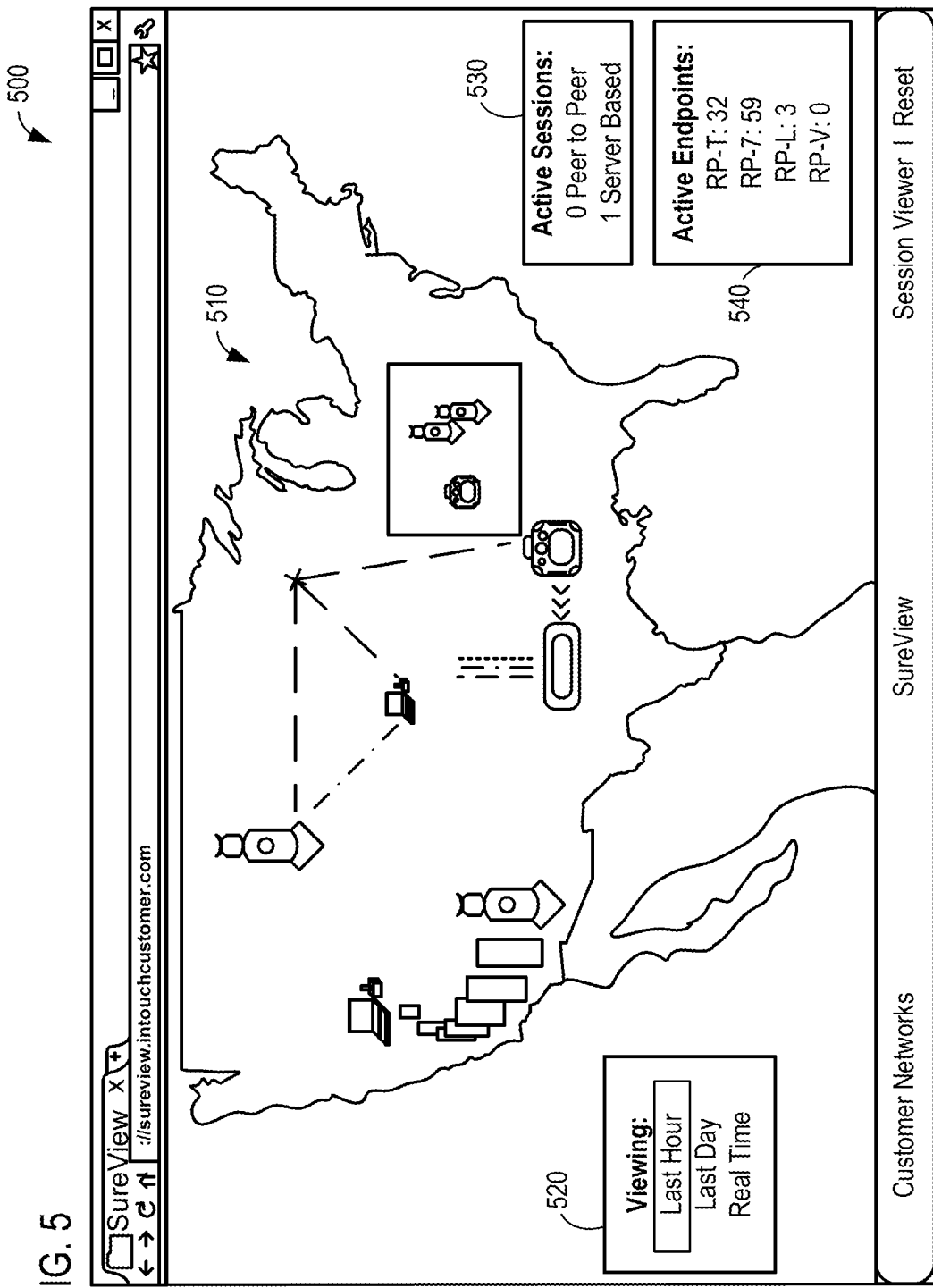
FIG. 5 illustrates a viewing level including a session viewer for monitoring sessions and telepresence devices during a selected time period.

FIG. 5 illustrates a viewing level 500 including a session viewer for visualizing and/or managing sessions and telepresence devices during a selected time period. The session viewer viewing level 500 may allow a user to visualize data relating to specific remote telepresence sessions on a geographic representation 510. The visualization may include a set of lines or arcs representing the connections. As illustrated, a time period may be selected in panel 520, the total number of active sessions may be illustrated in the active session panel 530, and the active telepresence devices (endpoints) may be illustrated in panel 540. Icons representing various telepresence devices, healthcare facilities, and/or communication connections may be displayed on the geographical representation 510, as illustrated in FIG. 5.

In various embodiments, visual attributes and/or text associated with the communication connections may be indicative of a telepresence session's quality, control station used, servers used, and/or other session data. For example, the visual appearance of a communication connection may be modified based on the session's quality, the control station, which server was used to negotiate the connection, the endpoint, the type of session (peer-to-peer or server-based), and/or other session data. A single session, a set of sessions from multiple endpoint and control station pairs at a single point in time, and/or a set of multiple sessions over a time span specified by the user may also be provided in this or another viewing level.

In various embodiments, a viewing level including a session viewer as illustrated in FIG. 5 may allow a user to view the number of active sessions, a list of active telepresence devices, and filtering options to limit the types of devices displayed, the connection types, the server types, the time period, and/or other attributes of telepresence sessions. In some cases, a user may view session data associated with a particular mobile telepresence unit. The visualization and management system may display a geographical representation bounded by a travel area of the mobile telepresence unit.

Figure 6:
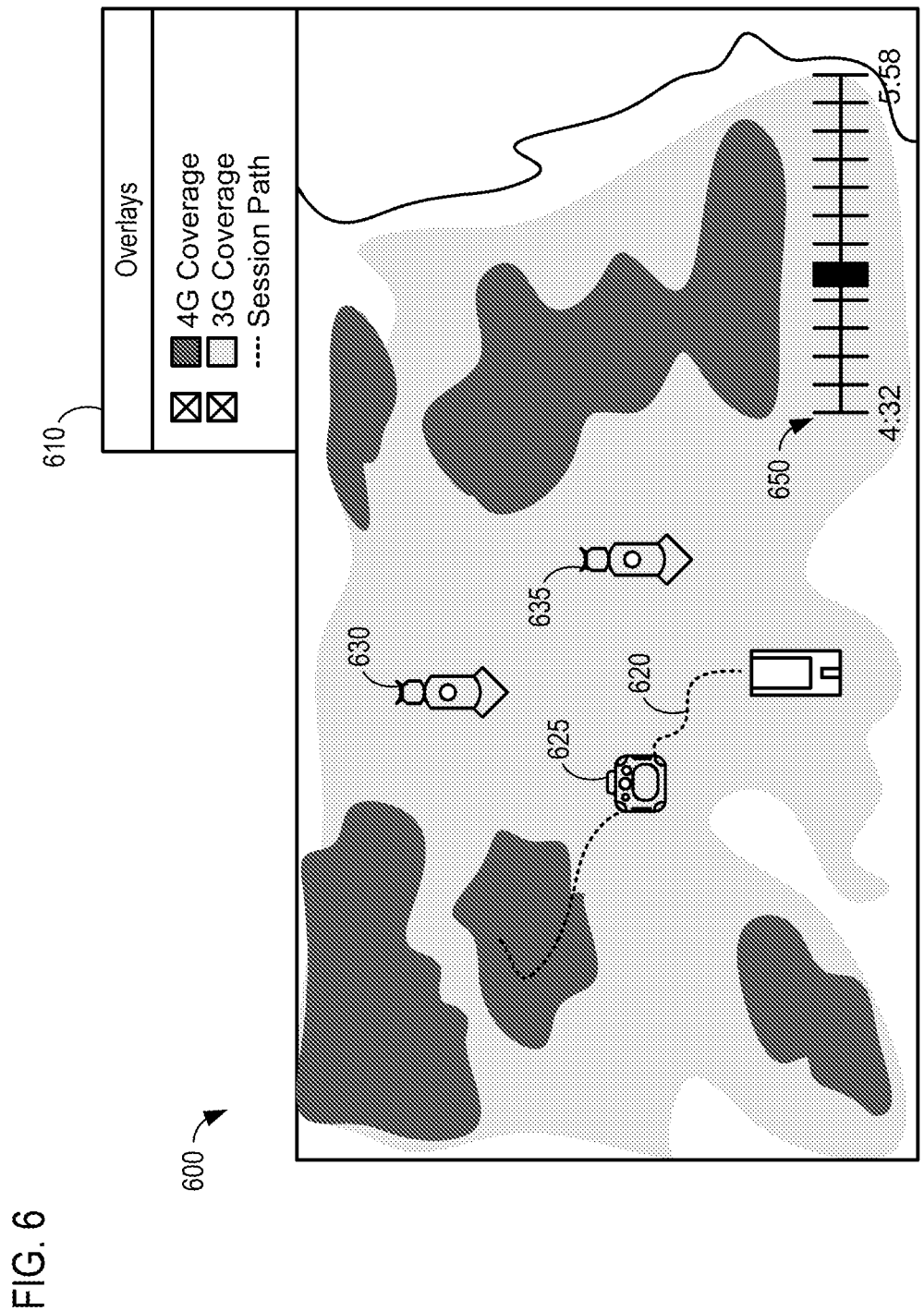
FIG. 6 illustrates a detailed session viewer for monitoring a location of a telepresence device at various time periods on a geographical representation, the geographical representation including an overlay of wireless communication availability.

As illustrated in FIG. 6, various overlays may be used in conjunction with the session viewer viewing level in order to provide additional information about a particular telepresence session. A viewing level 600 may include a route 620 traveled by a mobile telepresence device 625 over a given time period. The viewing level 600 may also include robot telepresence devices 630 and 635 with which the mobile telepresence device 625 communicated. The relative location of the mobile telepresence device 625 may move along the route 620 as the time is moved along the timeline 650 from 4:32 to 5:58 (corresponding to the beginning and end of one or more telepresence sessions).

An overlay, such as 3G and 4G cellular data availability, may be selected from panel 610 and overlaid on the geographical representation of the viewing level 600 in order to provide additional information to the user. The user may diagnose communication problems and/or improve the overall telepresence session experience using various informational overlays. Such a viewing level may be particularly useful for visualizing and/or managing the use of mobile telepresence units transported in ambulances and/or used remotely by healthcare practitioners (e.g., while at home or on vacation). For example, while monitoring a number of active sessions in a session viewer as illustrated in FIG. 5, a user may see an indication of a connection problem associated with a mobile telepresence device. In response, the user may open a session viewer associated with the mobile telepresence device, as illustrated in FIG. 6, and chose to overlay 3G and/or 4G cellular data availability to investigate and discover possible causes of the connection problem.

Figure 7A:
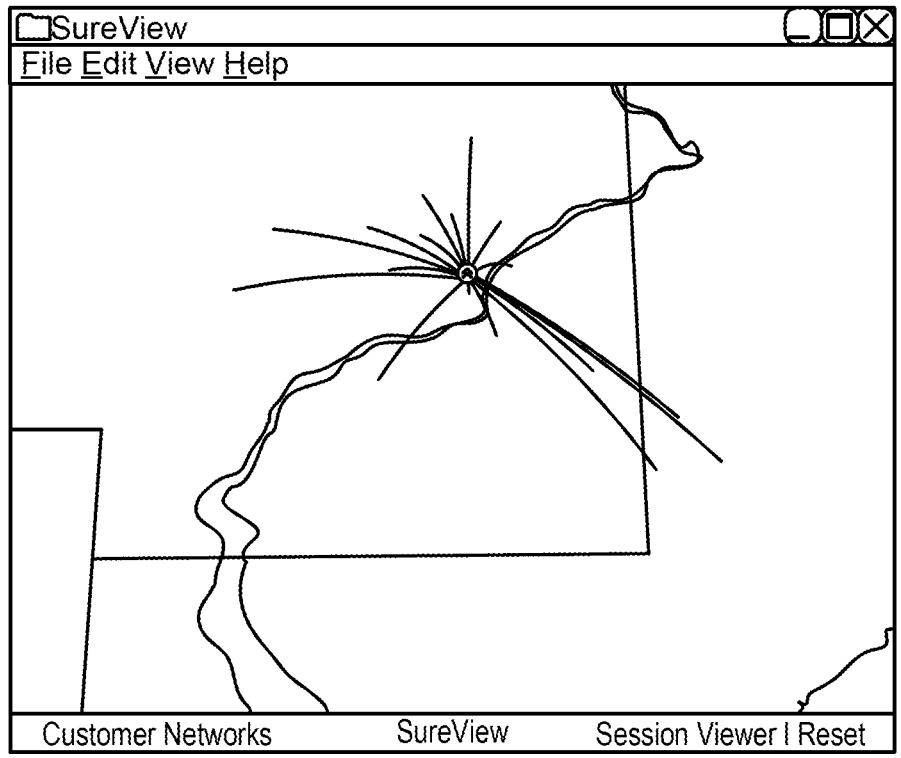
FIGS. 7A and 7B illustrate viewing levels including the location and interconnections of medical facilities in a healthcare network on a geographical representation.

As described in conjunction with FIG. 1, a user may select a viewing level that displays the relative location of at least one healthcare facility and its relationships to other healthcare facilities on a geographical representation. FIG. 7A illustrates a hub healthcare facility, such as a hub hospital, and its relationships with other healthcare facilities as arcs extending from the hub healthcare facility to other related healthcare facilities on a geographical representation. Transitioning to the viewing level 700 may initially remove all telepresence device icons and display a new set of icons representing each customer organization. Different icons may be used to represent each type of healthcare facility and/or the capabilities of each healthcare facility. Additionally, different icons may be used to represent various classes of customers, such as hospitals, clinics, corporate headquarters, partner hospitals, and others. Similar to the description above, hovering over a customer icon may display the organization's name and/or some additional information. Clicking on a customer icon may display all the telepresence devices and/or hospitals associated with the customer's network. Animated arcs representing the current connectivity paths may extend from the customer hub or headquarters to the locations of current telepresence devices.

Figure 7B:
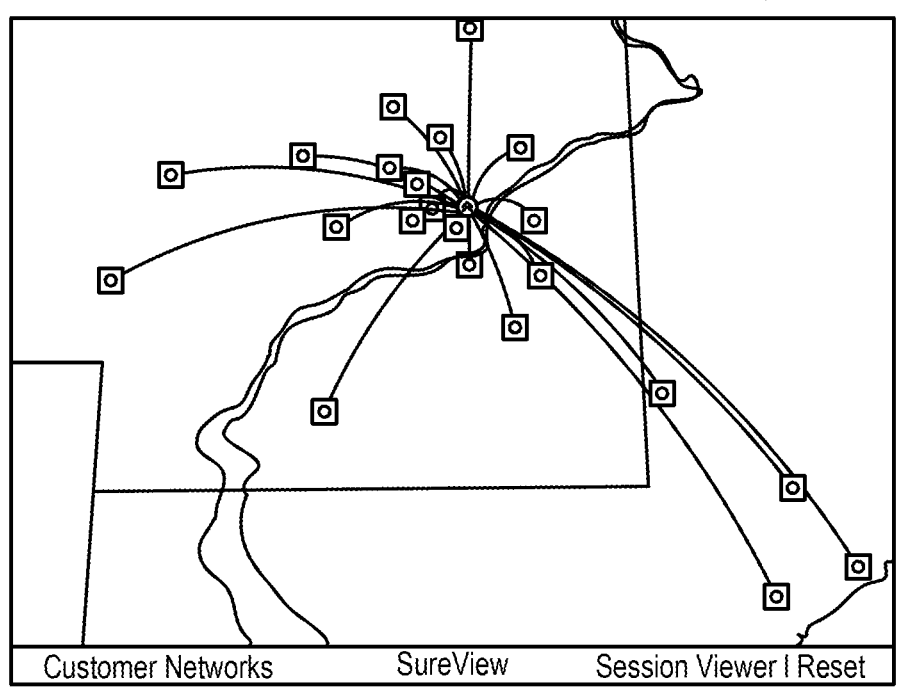

Additional details about arc connections and/or the hub hospital may be made available to a user by selecting or mousing over the icons. FIG. 7B illustrates a viewing level 750 including the location and interconnections of various healthcare facilities in a healthcare network on a geographical representation. Again, context-sensitive detail requests may be made by mousing over the healthcare facilities and/or the connections therebetween.

Additional viewing levels may include menus, icons, and/or other information for visualizing and/or managing the connectivity between various telepresence devices, healthcare practitioners, healthcare facilities, and/or healthcare networks. Additionally, details regarding how and when patients are transferred between various healthcare facilities may be presented as numerical values, as statistics, as graphs, and/or geographically on a geographical representation. In some embodiments, specific viewing levels may be available that display details associated with the shipment history of particular devices and/or software/firmware updates associated with one or more telepresence devices.

For example, a viewing level may include the shipment history of a telepresence device with respect to a timeline. The location of the telepresence device may be visualized at each point during the shipment process. Such a viewing level may allow for the optimization of transportation and shipping of telepresence devices. A viewing level may also be configured to illustrate the progress of an automatic software update from release time to some threshold of acceptance among the telepresence devices in a particular geographical area. For example, a software update is generally released to the entire fleet at a certain time and date. A telepresence device may be automatically updated when it connects to the network. The threshold of acceptance may be when 95% of all telepresence devices have reported that the new update has been installed. The viewing level may provide for the visualization of a software update on a geographical representation. For example, all telepresence devices may initially start with a red circle in their icon to show they have not accepted the update. As the user advances a time bar forward from the release date, the telepresence device icons may change color to show the status of a software update process. This might be from red (not installed) to yellow (downloading from a server) to green (installed). Accordingly, a user may gauge the effectiveness of an automatic software update system. This visualization tool may allow a user to easily identify areas, or specific telepresence devices, where the update process failed or encountered problems.

Figure 8:
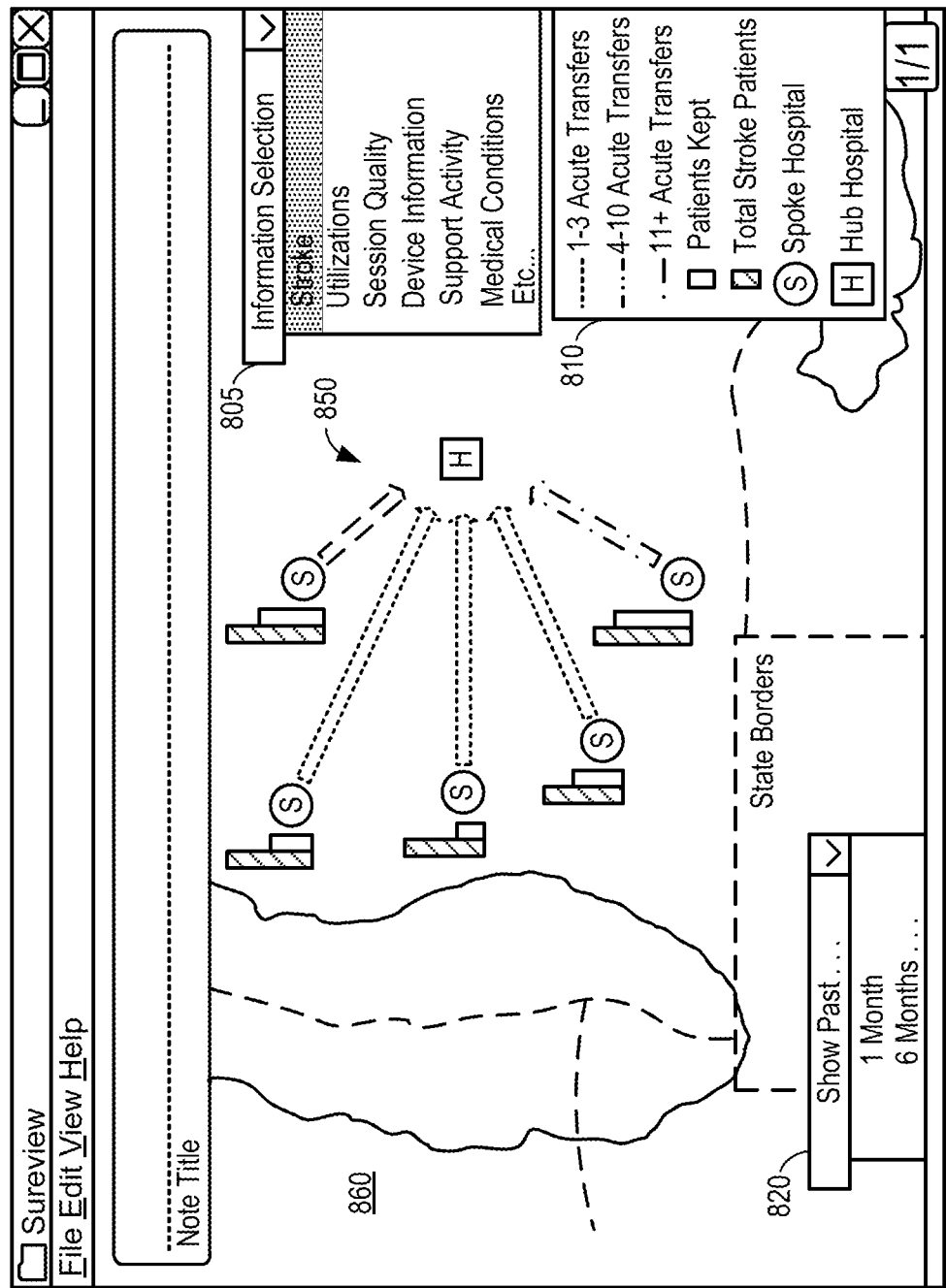
FIG. 8 illustrates a viewing level providing stroke information associated with a healthcare network on a geographical representation.

As illustrated in FIG. 8, a viewing level 800 may display information associated with a healthcare network 850 on a geographical representation 860. A timeline filter may be provided in a panel 820. Viewing level 800 may include an information selection panel 805. Viewing level 800 allows information 805 associated with multiple healthcare facilities 810 and/or telepresence devices to be visually presented in conjunction with a geographical representation 860. A user may select between a variety of informational overlays, graphs, informational tags, icons, text, numbers, connection lines, and/or colors to visually convey information related to healthcare facilities and/or telepresence devices. According to various embodiments, a user may graphically compare data among spoke healthcare facilities or between spoke healthcare facilities and a hub healthcare facility (see key 810) on the geographical representation 860.

In the illustrated embodiment, stroke information has been selected in the information selection panel 805. Accordingly, a user may view the number of patients who were the subject of a stroke consultation made by a healthcare practitioner in a hub healthcare facility using telepresence devices. A user may view the number of such patients who were determined fit to stay in the rural (spoke) healthcare facilities, and those who were transferred to the more capable hub healthcare facility. Such a viewing level may allow for a visualization of the effectiveness and results of consultations via telepresence devices.

The viewing level 800 may allow a user to visualize the value a telepresence system is bringing to a customer's hub hospital and spoke hospitals in terms of patients kept and acute cases transferred. For example, a rural hospital's administrator may visualize the number of patients who were subject to a telepresence consultation performed by a specialist based in a hub hospital. The rural healthcare facility may have a small graph beside it indicating the number of patients kept versus the total number of stroke patients admitted in the selected time period. The healthcare facility may also have an arrow configured with a width corresponding to the relative number of patients transferred from the spoke healthcare facility to the hub healthcare facility. Accordingly, the rural hospital administrator (and the hub hospital administrator) may visualize the benefits of the telepresence devices and telepresence network.

The user may select a different information set from information selection panel 805 in order to visualize data relating to a particular facility or device, or visually compare data between and/or among various spoke and hub healthcare facilities 810 on the geographical representation 860. Additionally, information directly related to the telepresence devices may be selected within information selection panel 805, in order for a user to visually compare the status of telepresence devices between spoke healthcare facilities 810 on the geographical representation 860. Information sets selectable via information selection panel 805 may include, but are not limited to, information related to medical condition, such as stroke or heart attack, utilization rates, session quality information, telepresence device information, support activity, battery levels, last reported time, active session, workflow metrics, available telepresence devices, trained specialists, financial information, subscription information, and/or other information associated with telepresence devices, telepresence networks, healthcare facilities, and/or healthcare networks.

Figure 9:
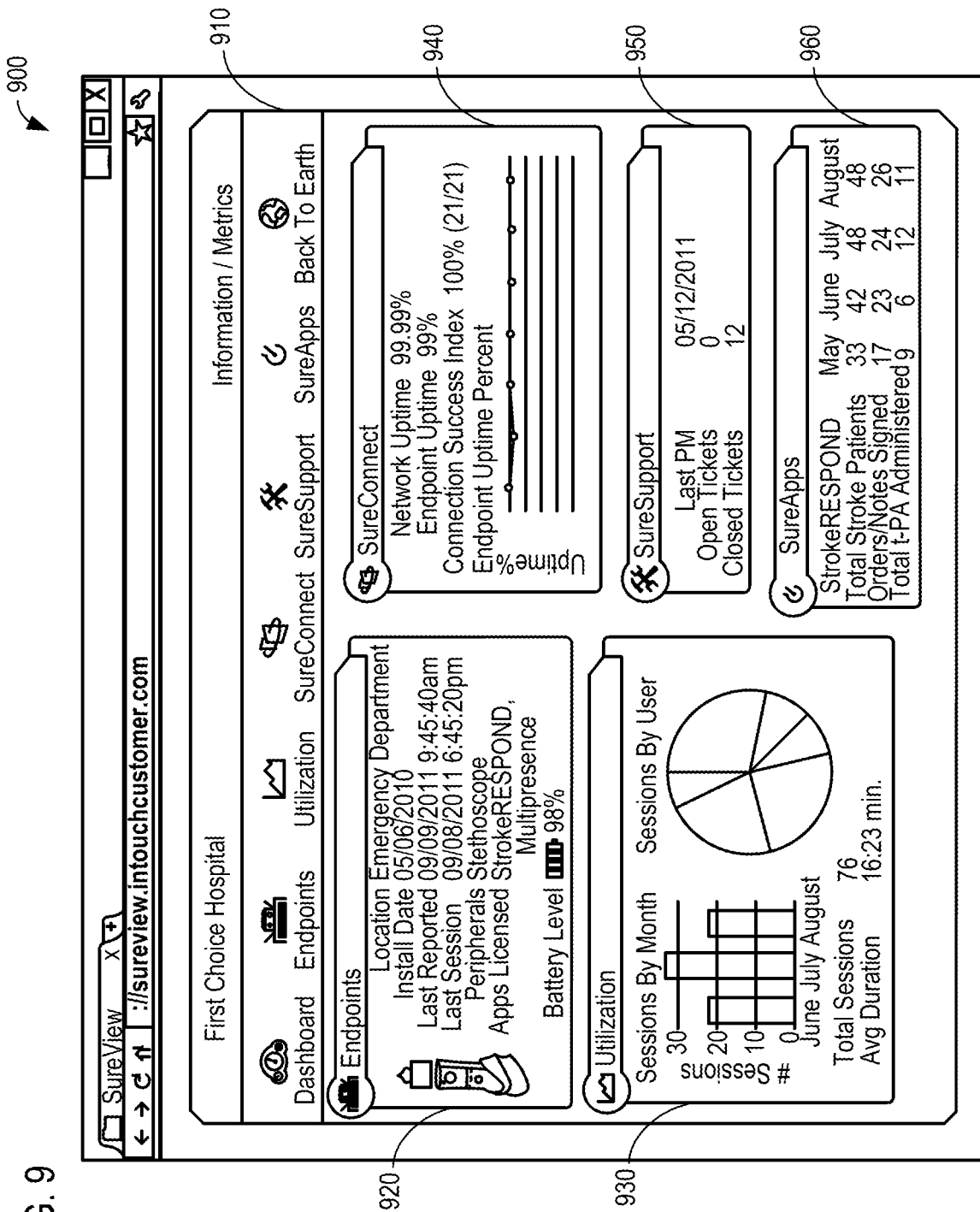
FIG. 9 illustrates a viewing level including a dashboard of detailed information associated with one or more telepresence devices.

FIG. 9 illustrates a viewing level 900 including a dashboard of detailed information 920, 930, 940, 950, and 960 associated with one or more telepresence devices. The displayed details may include various numerical information, charts, and/or graphs. The information displayed in the dashboard of information may depend on the types of telepresence devices, the types of healthcare facilities, and/or the identity of the user. A navigation bar 910 may allow the user to navigate between various viewing levels. In the illustrated example, an endpoint panel 920 may include details associated with one or more endpoints (telepresence devices) in a healthcare facility. Endpoint panel 920 may include real-time information associated with a particular telepresence device, including, but not limited to, a serial number, model number, type, name, battery level, connection status, location, date and time last reported, available peripherals, and associated applications.

A utilization panel 930 may display details associated with the remote telepresence sessions for one or more telepresence devices and/or a particular healthcare facility or network. For example, the utilization panel 930 may include details regarding utilization over various time periods, a total utilization time, an average session duration, a duration of a particular session, a start time and end time of a particular session, a Quality of Service (QoS) for one or more sessions, a current available bandwidth, a bandwidth availability with respect to time, a current location of a telepresence device, and historical locations of a telepresence device with respect to time.

Support panel 950 may display information associated with technical support, software updates, firmware updates, hardware updates/replacements, and/or other support issues. Support panel 950 may display a list of personnel responsible for a telepresence device and/or healthcare facility. Historical data regarding support issues may also be available. Automatic and/or manual updates may be applied via support panel 950 as well.

An application panel 960 may provide information associated with applications registered for use with the telepresence device and/or healthcare facility. Information associated with various workflow applications, such as StrokeRESPOND described in U.S. Patent Application 2010/0191375, which application is hereby incorporated by reference in its entirety, may also be displayed or made accessible in application panel 960.

A connection panel 940 may include information associated with network connections and maintenance. For instance, connection panel 940 may display the basic network start and end times and durations of network connectivity. Connection panel 940 may include a graphical representation of network up-time, network down-time, bandwidth availability, bandwidth use, max ping, average ping, packet loss, and/or other information associated with network connectivity between a telepresence device and a healthcare facility. Network information associated with a connection between two healthcare facilities may also be displayed and/or managed.

Connection panel 940 may additionally, or alternatively, display information associated with connection services configured to provide a reliable and robust peer-to-peer and/or server-based connection across a wide range of network types. For instance, the systems and methods described in U.S. Patent Application 2008/0281467, which application is hereby incorporated by reference in its entirety, may be used in conjunction with the presently described systems and methods. Connection panel 940 may also display information associated with automatic bandwidth tests and/or general profiling of a network.

Figure 10:
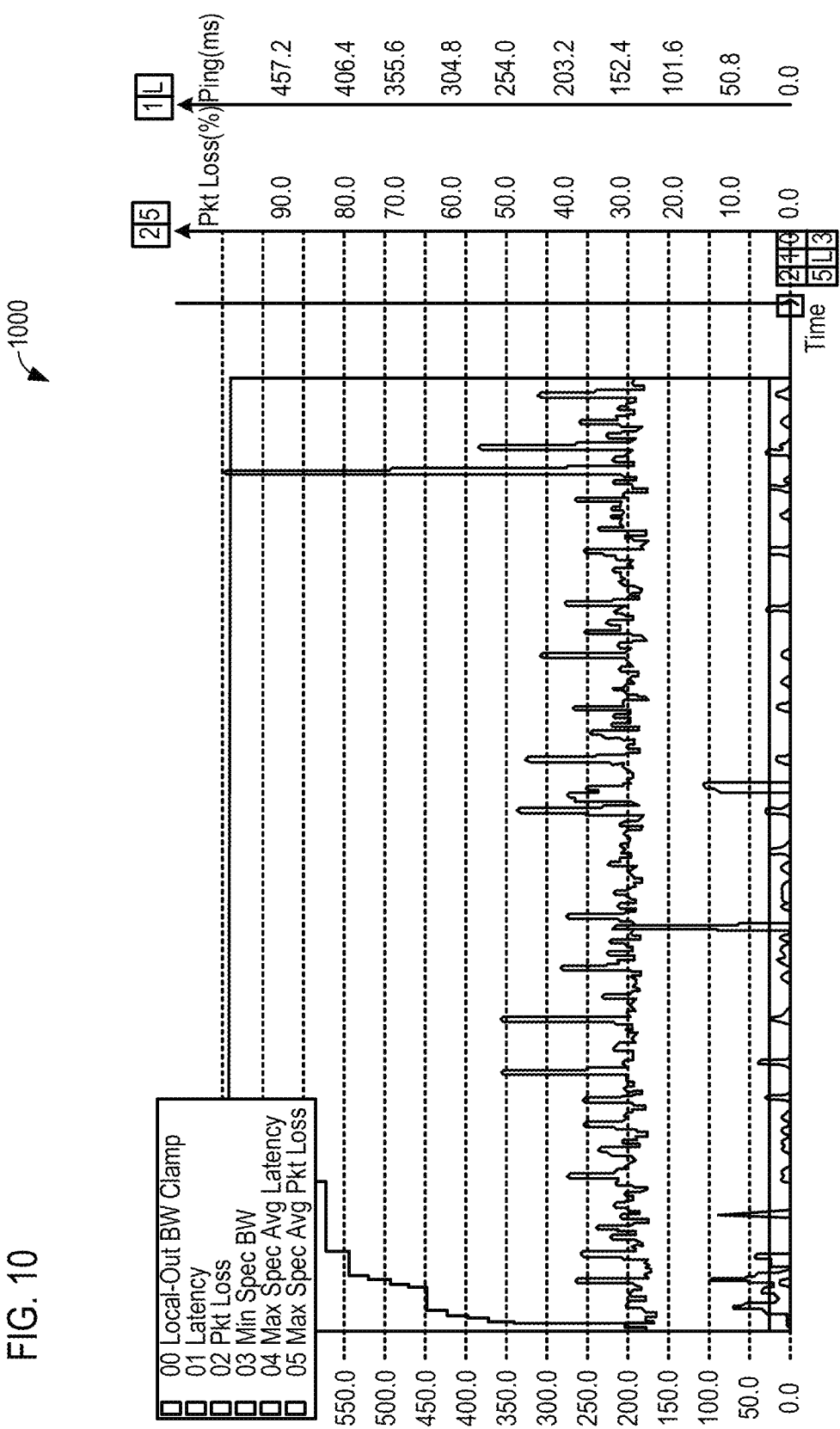
FIG. 10 illustrates a viewing level including session details for a particular telepresence device.

FIG. 10 illustrates a viewing level 1000 displaying the dynamic bandwidth management, latency, and packet loss during various time periods for one or more telepresence devices. Such a viewing level 1000 may be useful for a user to diagnose networking problems and/or improve a telepresence network.

Figure 11:
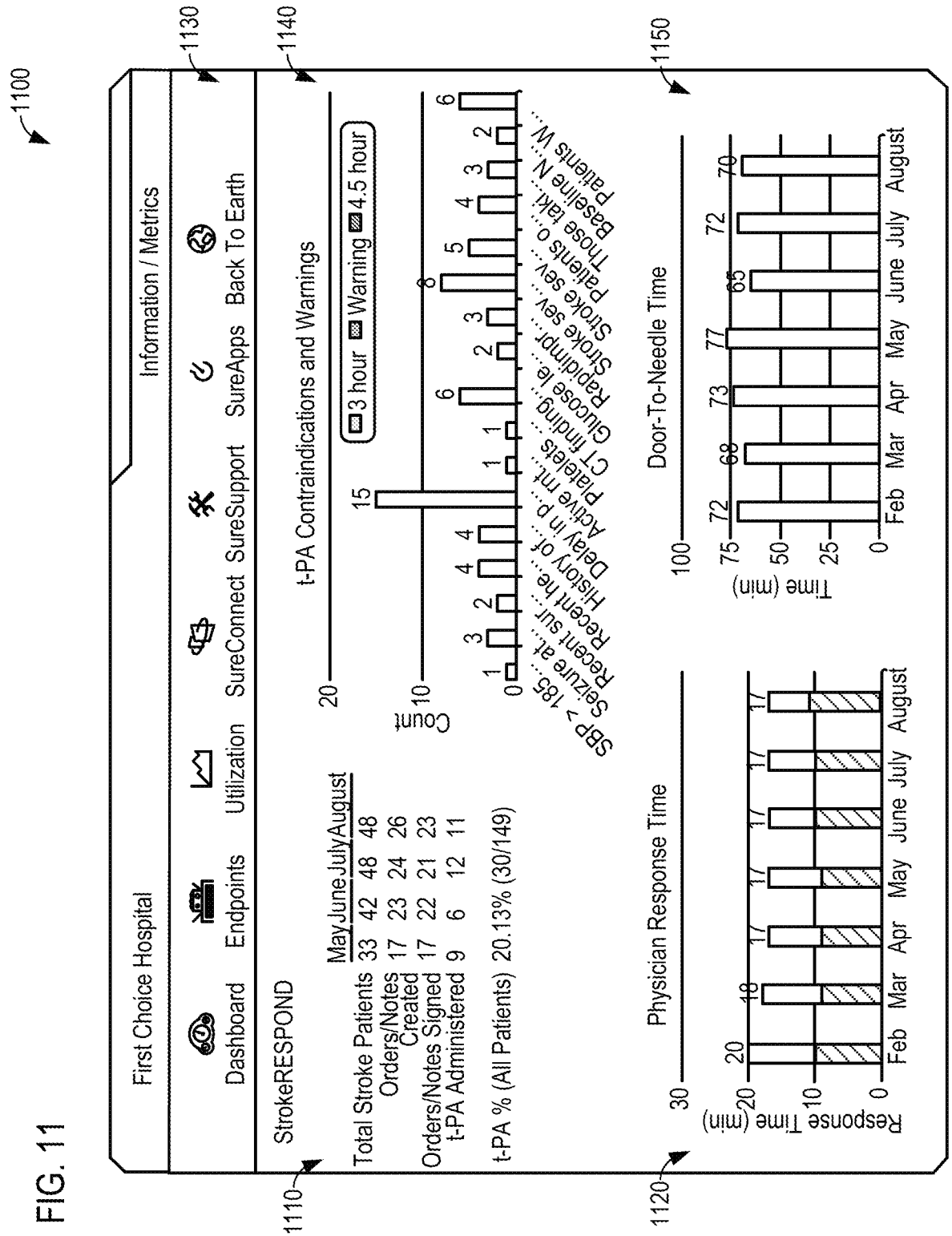
FIG. 11 illustrates a viewing level including stroke information associated with a healthcare network provided via a StrokeRESPOND application.

FIG. 11 illustrates a viewing level 1100 of an application selected via application panel 960 in FIG. 9. The exemplary information panels illustrated in FIG. 11 are associated with the application StrokeRESPOND. Any of a wide variety of application interfaces may be accessible via the visualization and management system described herein. As illustrated, information associated with strokes may be displayed in conjunction with the StrokeRESPOND application. For instance, the display may include a door-to-needle time 1150 corresponding to the amount of time between a patient's arrival at a healthcare facility and the time the patient receives clot-busting medication. The display may also include StrokeRESPOND statistics 1110, physician response times 1120, and/or t-PA contraindications and warning information 1140. A user may navigate to alternative viewing levels and/or return to the previous viewing level via panel 1130.

Figure 12:
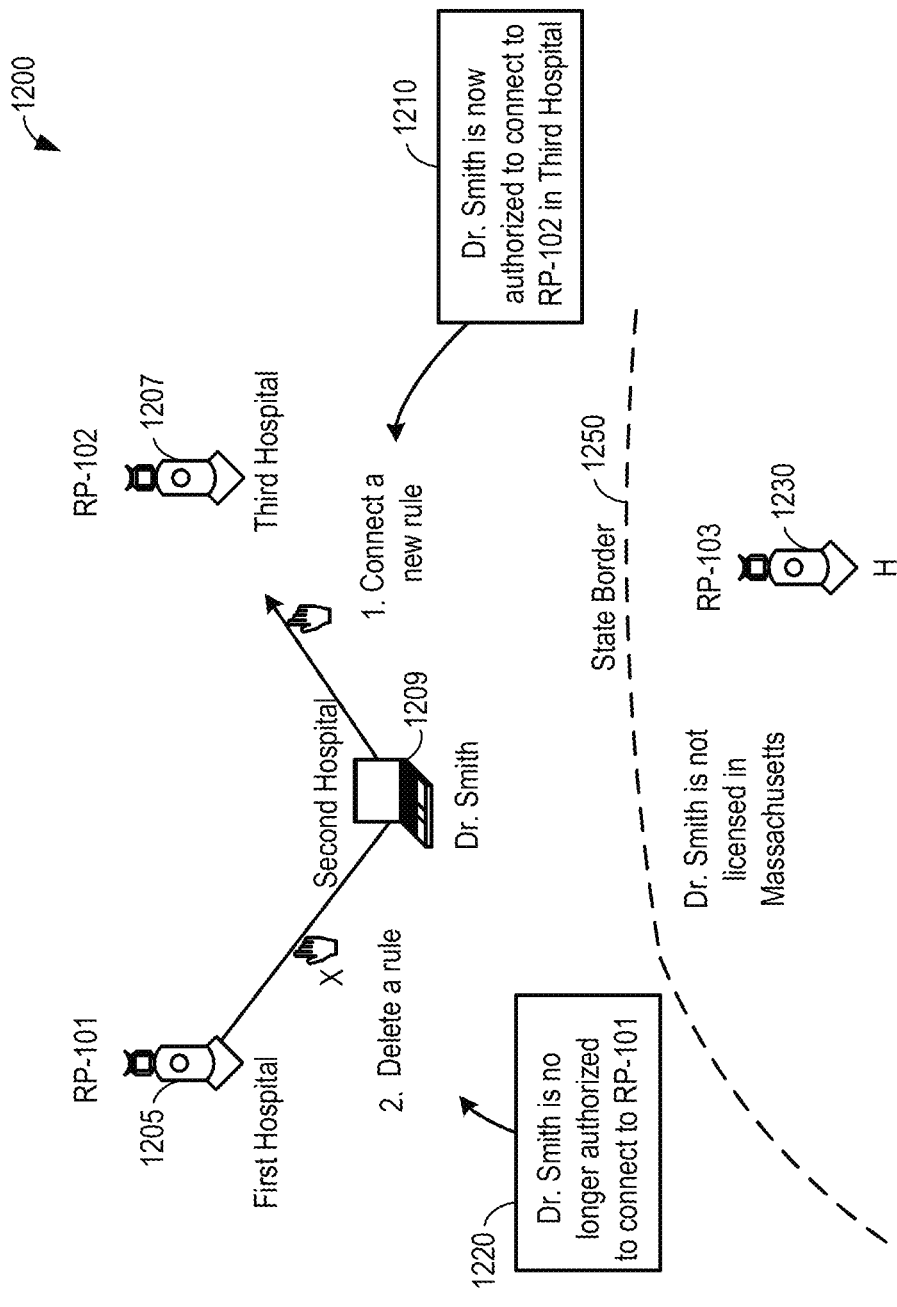
FIG. 12 illustrates a viewing level allowing for the management of connection rules between healthcare practitioners, healthcare facilities, and telepresence devices.

According to various embodiments, a user may select a viewing level 1200 allowing for the management of connection rules between telepresence devices, healthcare facilities, and/or healthcare practitioners, as illustrated in FIG. 12. Connection rules may be managed using any of a wide variety of systems and methods, including those described in U.S. Patent Applications 2010/0131102 and 2010/0131103, which applications are hereby incorporated by reference in their entireties.

As illustrated, a control station 1209 may be accessible to a Dr. Smith. An existing connection rule allows Dr. Smith to access telepresence device RP-101 in First Hospital 1205. By deleting this connection rule, at 1220, Dr. Smith will no longer be authorized to connect to RP-101 in First Hospital 1205. By drawing a connection rule between the control station 1209 in Second Hospital and RP-102 in Third Hospital 1207, a new connection rule authorizes Dr. Smith to connect to RP-102 in Third Hospital, at 1210.

The visualization and management system may recognize the state border 1250 and that Dr. Smith is not licensed in Massachusetts. Accordingly, the visualization and management system may prevent a connection rule from authorizing Dr. Smith to access RP-103 in Massachusetts 1230. Similar management methods may be used to manage connection rules between any combination of healthcare practitioners, healthcare facilities, telepresence devices, and/or other users. As illustrated, a user may easily visualize and manage various connection rules using the systems and methods described herein. Specifically, the drag-and-drop methods described above provide for intuitive management of complex connection rules between a large number of healthcare practitioners, healthcare facilities, and/or telepresence devices.

Figure 13:
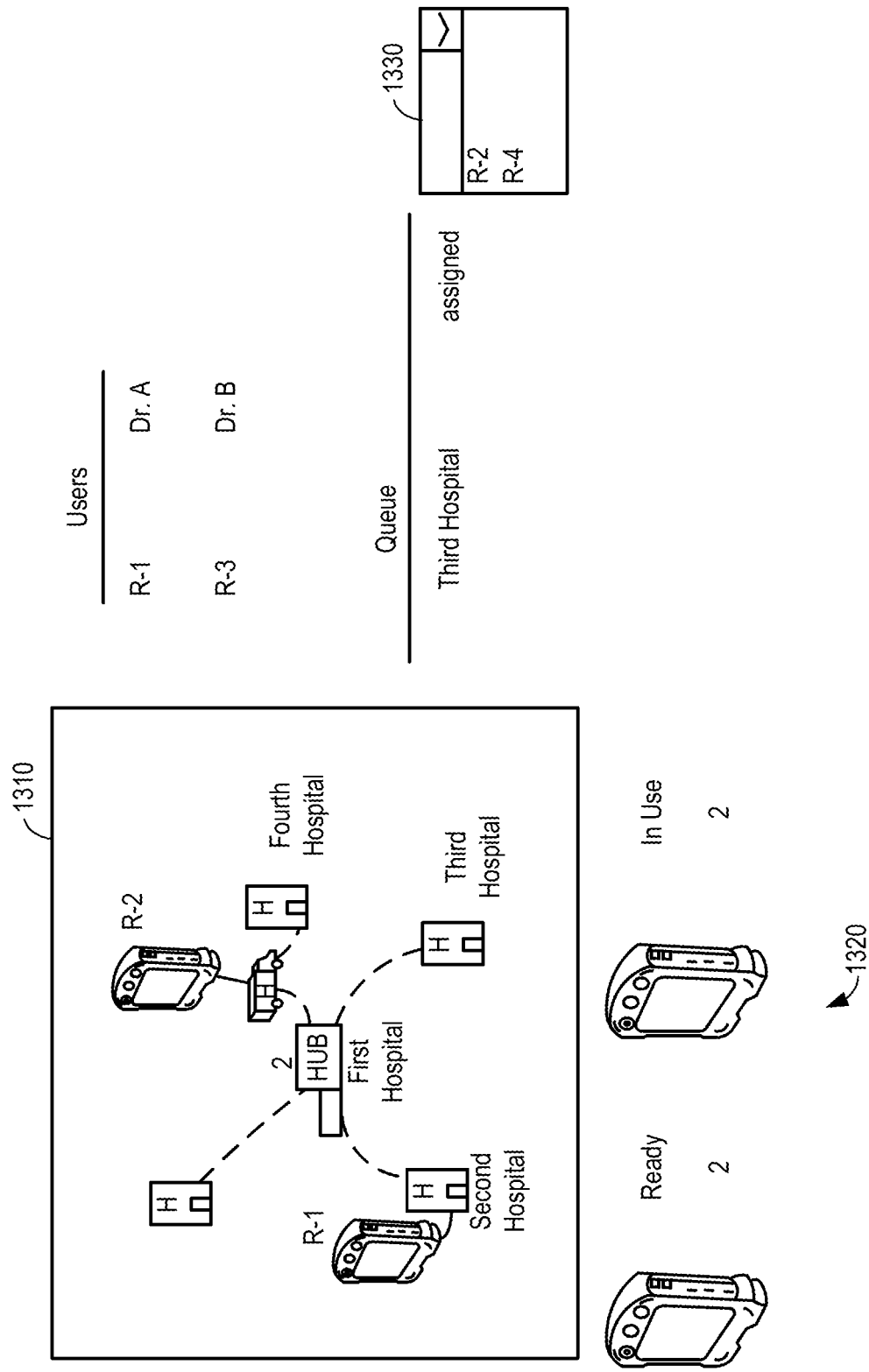
FIG. 13 illustrates a viewing level configured to allow for the management of the usage of the telepresence devices with a geographical visualization tool.

FIG. 13 illustrates another viewing level 1300 accessible to a user. The viewing level 1300 may display the relative location of a number of telepresence devices 1310 and 1320. The viewing level 1300 may include a transfer center interface for managing mobile telepresence units 1310 and 1320. The user may track the geographic location of various mobile telepresence units and determine which units are in use 1310, who is using them, and when they are scheduled to be available. Accordingly, user may manage a queue 1330 of mobile telepresence units.

Figure 14:
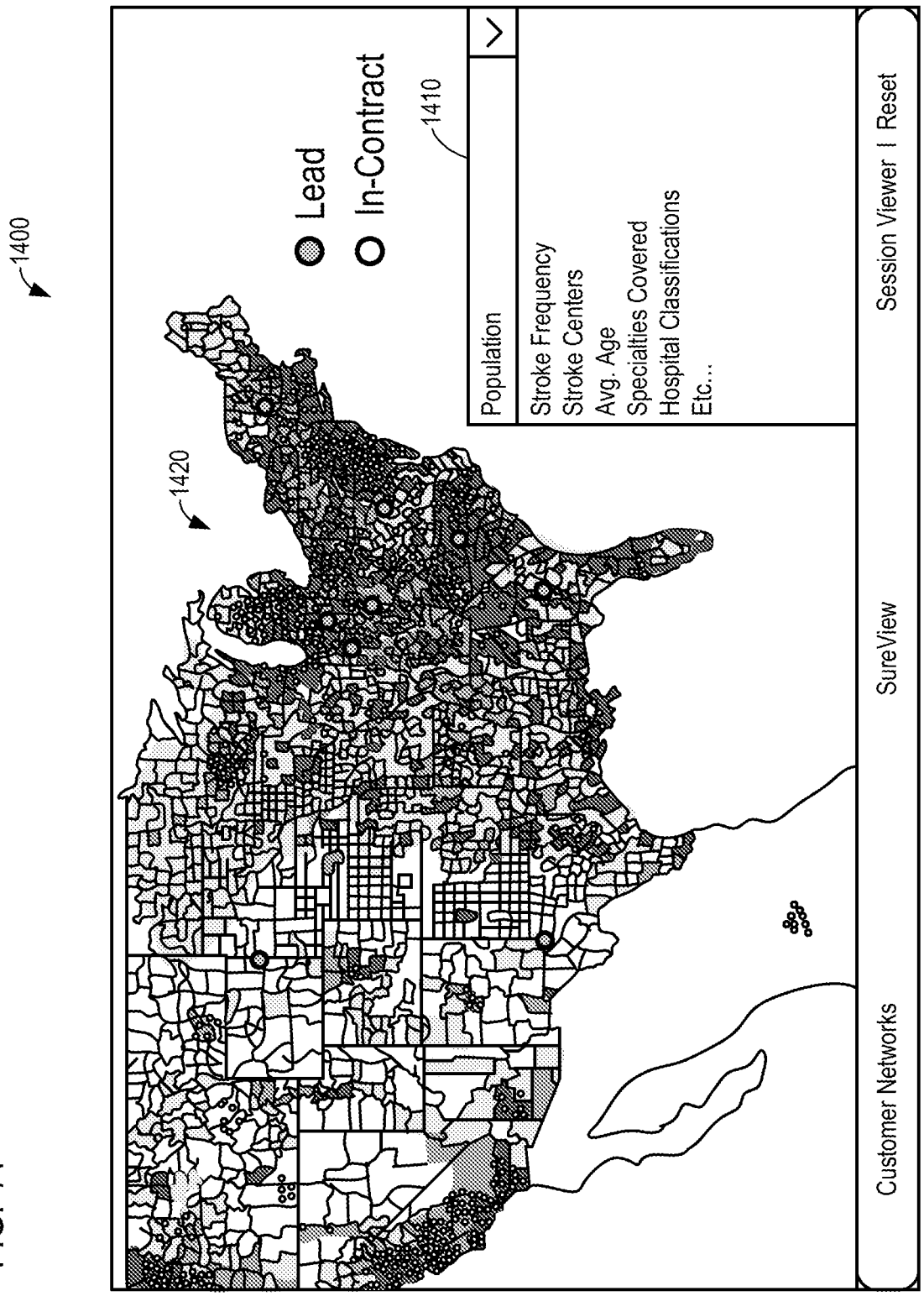
FIG. 14 illustrates a viewing level including a geographical representation of the United States with an overlay of information associated with a potential need for telepresence devices.

FIG. 14 illustrates a viewing level 1400 that may be useful for identifying a need for additional telepresence devices. The illustrated viewing level 1400 may include a geographical representation 1420 of the United States. The geographical representation 1420 may be overlaid with a population density heat map, a stroke frequency heat map, an average age heat map, an availability of a particular medical specialty, hospital classifications, and/or other medical or demographical information. Additionally, the locations of existing telepresence device contracts and/or sales leads may be displayed as white dots on the geographical representation 1420. The overlays may be selectively toggled within overlay panel 1410. A user may utilize the visualization tools to identify needs and/or prospective sales opportunities.

Figure 15:
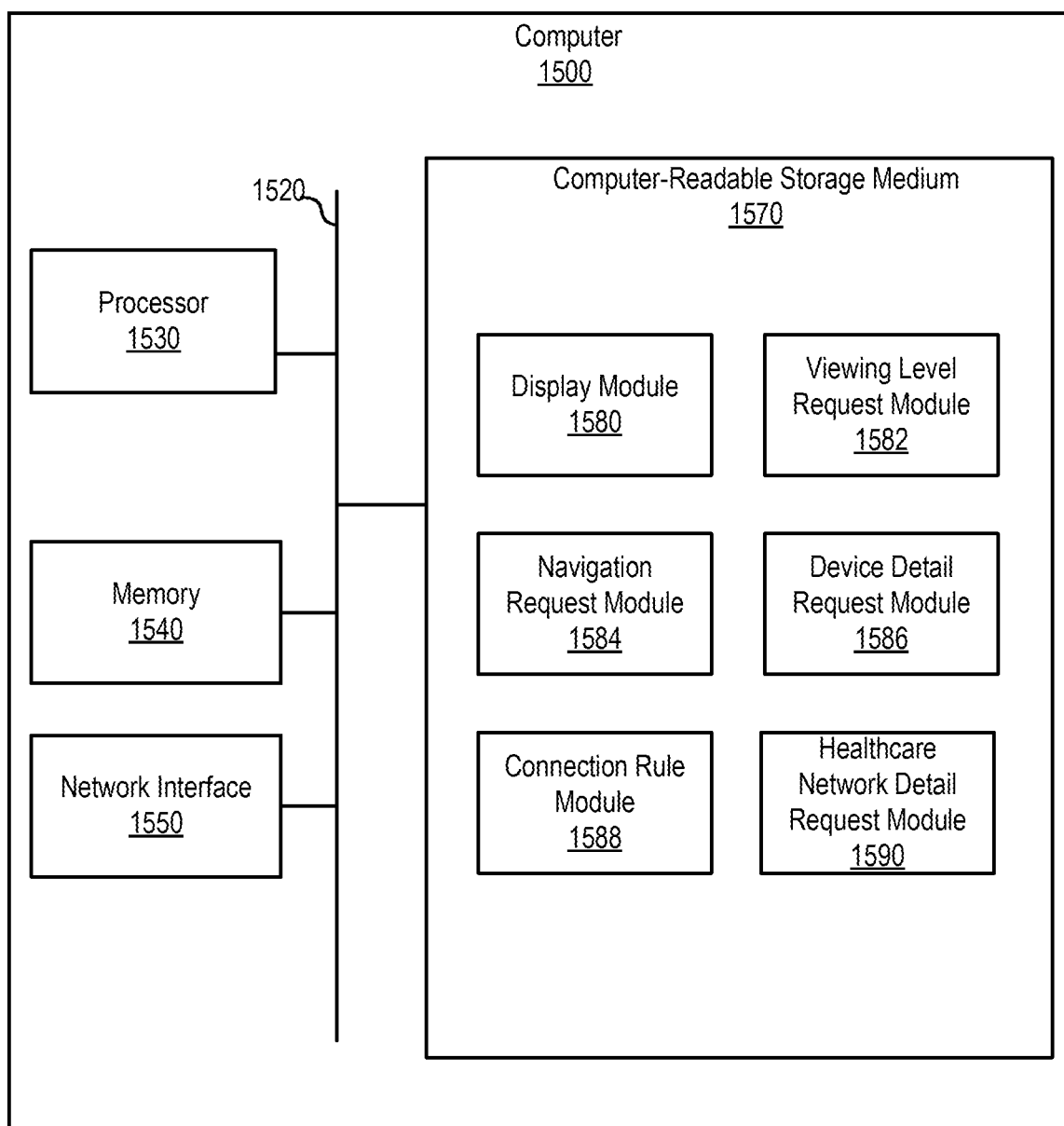
FIG. 15 illustrates a functional block diagram of a computer system including various modules for a telepresence network visualization and management system.

FIG. 15 illustrates a functional block diagram of a computer system 1500 including various modules 1570 for a telepresence network visualization and management system. As illustrated, computer system 1500 may include a processor 1530, memory (such as RAM) 1540, and a network interface 1550 connected via a bus 1520. The bus 1520 may also connect a computer-readable storage medium 1570. The computer-readable storage medium 1570 may include various modules, such as a display module 1580, a viewing level request module 1582, a navigation request module 1584, a device detail request module 1586, a connection rule module 1588, and a healthcare network detail request module 1590. Additional modules may be included, or some modules may be omitted, in order for a computer system to perform any of the server-side or client-side functions of the various systems and methods described herein.

The display module 1580 may be configured to display a viewing level of a telepresence network on a geographical representation. The viewing level request module 1582 may be configured to receive a viewing request to cause the display module 1580 to provide a second viewing level. The navigation request module 1584 may be configured to receive a navigational request to navigate within the geographical representation. The device detail request module 1586 may be configured to receive a detail request to cause the display module 1580 to display a third viewing level, the third viewing level including information associated with one or more telepresence devices. The connection rule module 1588 may be configured to allow for the management of a connection rule governing telepresence devices. The healthcare network detail request module 1590 may be configured to receive a healthcare network detail request to cause the display module 1580 to display a fourth viewing level, the fourth viewing level including information associated with healthcare facilities.

Many changes may be made to the details of the above-described embodiments without departing from the underlying principles and scope of the present disclosure. Accordingly, the scope of the presently described systems and methods should be determined only by the following claims.

What is claimed:

1. A system for managing a telepresence network, comprising:
a display module configured to display a first viewing level of a telepresence network, the first viewing level comprising a graphical representation of a plurality of telepresence devices located within at least one healthcare facility, each of the plurality of telepresence devices being located in the vicinity of at least one patient within the at least one healthcare facility and configured to establish a session with a remote device during which a user of the remote device provides services to the at least one patient in the healthcare facility;
a detail request module configured to receive a selection of one of the plurality of telepresence devices and to display a second viewing level that includes a graph depicting a number of sessions conducted with the selected telepresence device.

2. The system of claim 1, wherein the first viewing level further comprises a representation of interconnections between a hub telepresence device and at least one endpoint telepresence device.

3. The system of claim 1, wherein in at least one viewing level an information selection module is configured to receive an information request; and wherein information associated with at least one of the plurality of telepresence devices or the at least one healthcare facility is displayed on the graphical representation corresponding to the information request.

4. The system of claim 3, wherein the information is associated with one of a medical condition, telepresence network utilization information, telepresence session quality information, telepresence device information, support activity, battery levels, currently active session, workflow metrics, available telepresence devices, trained specialists, financial information, and subscription information.

5. The system of claim 1, wherein each of the plurality of telepresence devices comprises one of a remote telepresence robot, a mobile telepresence unit, and a control station.

6. The system of claim 1, wherein the information associated with at least one of the plurality of telepresence devices displayed in the second viewing level comprises the number of active sessions associated with the at least one of the plurality of telepresence devices.

7. The system of claim 1, wherein the information associated with at least one of the plurality of telepresence devices displayed in the second viewing level comprises the connection strength associated with the at least one of the plurality of telepresence devices.

8. The system of claim 1, wherein the information associated with at least one of the plurality of telepresence devices displayed in the second viewing level comprises a connection rule of the at least one of the plurality of telepresence devices.

9. The system of claim 8, further comprising a connection rule management module configured to allow for the management of a connection rule of the at least one of the plurality of telepresence devices in the second viewing level.

10. The system of claim 9, wherein the connection rule management module is configured to allow for drag-and-drop connection rule management.

11. The system of claim 1, wherein the information associated with at least one of the plurality of telepresence devices displayed in the second viewing level comprises information pertaining to one of a software update and a firmware update of the at least one of the plurality of telepresence devices.

12. The system of claim 1, wherein the information associated with at least one of the plurality of telepresence devices displayed in the second viewing level comprises information pertaining to one of a serial number, a model number, a battery level, a location, a date the telepresence device last reported, a time the telepresence device last reported, historical session data, a registered peripheral, a licensed application, a total utilization time, an average session duration, a duration of a particular session, a start time of a particular session, an end time of a particular session, a Quality of Service (OoS) for one or more sessions, a current available bandwidth, and a bandwidth availability with respect to time.

13. The system of claim 1, wherein the first viewing level comprises a graphical representation of at least one hub hospital having at least one telepresence device, each hub hospital connected to at least one spoke hospital having at least one telepresence device.

14. The system of claim 13, wherein in the first viewing level an information selection module is configured to receive an information request; and wherein information associated with at least one of the hospitals is displayed on the graphical representation corresponding to the information request.

15. The system of claim 14, wherein the information is associated with one of a medical condition, telepresence network utilization information, telepresence session quality information, telepresence device information, support activity, battery levels, currently active session, workflow metrics, available telepresence devices, trained specialists, financial information, and subscription information.

16. The system of claim 13, further comprising a healthcare network detail request module configured to receive a healthcare network detail request to cause the display module to display a third viewing level, the third viewing level displaying information associated with the at least one hub hospital and the at least one spoke hospital.

17. The system of claim 13, wherein receiving the healthcare network detail request comprises selecting one of the at least one hub hospital and the at least one spoke hospital.

18. The system of claim 13, wherein receiving a detail request comprises a mouse-over selection of one of the at least one hub hospital and the at least one spoke hospital.

19. The system of claim 18, wherein the information associated with one of the at least one hub hospital and the at least one spoke hospital displayed in the fourth viewing level comprises one of a number of active sessions, a number of active telepresence devices, a connection strength of telepresence devices, a connection between two or more telepresence devices, a location of a telepresence device, information from a StrokeRESPOND application, a door-to-needle time, a door-to-balloon time, a t-PA contraindication, a t-PA warning, a medical practitioner response time, and a call center response time.

20. The system of claim 19, wherein the information associated with one of the at least one hub hospital and the at least one spoke hospital displayed in the third viewing level is associated with one of a particular hospital, a network of hospitals, a medical practitioner, a telepresence device, a patient, and a geographical area.

* * * * *